United States Patent [19]

Levanova et al.

[11] Patent Number: 4,473,556

[45] Date of Patent: Sep. 25, 1984

[54] COMPOSITION AND METHOD FOR TREATING GASTROINTESTINAL DISTURBANCES IN ANIMALS AND METHOD FOR PRODUCING THIS COMPOSITION

[75] Inventors: Valentina P. Levanova; Valery P. Urban, both of Leningrad; Oleg D. Vasiliev, Leningradskaya; Emilia N. Gvozdeva, Leningrad; Leonid V. Dmitrenko, Leningrad; Igor I. Korolkov, Leningrad; Mikhail I. Kuznetsov, Leningrad; Inga S. Artemieva, Leningrad; Tamara A. Boiko, Leningrad, all of U.S.S.R.

[73] Assignee: Nauchno-Proizvodstvennoe Gidroliz-Noe Obiednenie, Leningrad, U.S.S.R.

[21] Appl. No.: 263,547

[22] Filed: May 14, 1981

[51] Int. Cl.$^3$ .................. A61K 35/78; A61K 31/70; A61K 37/00
[52] U.S. Cl. .................. 424/180; 424/195; 424/177; 260/124 R
[58] Field of Search .................. 424/180, 195, 177; 260/124

[56] References Cited

FOREIGN PATENT DOCUMENTS 556811 6/1977 U.S.S.R. .

OTHER PUBLICATIONS

*Chemical Abstracts*, vol. 74, 1971, p. 262, Abstract No. 115885n, Walfarm, S., "Lignin–Based Pharmaceuticals".

Sharkov et al., In Hydroliznaja 1, Lesohimicheskaja Promishlennost, No. 2 of 1979.

*Primary Examiner*—Delbert R. Phillips
*Assistant Examiner*—F. T. Moezie
*Attorney, Agent, or Firm*—Ladas & Parry

[57] ABSTRACT

Disclosed is a composition for treating acute gastrointestinal disturbances in animals, comprising lignin, hydrocellulose and mineral substances at the following ratio of said components in percent by mass:

| lignin | 38 to 78 |
|---|---|
| hydrocellulose | 20 to 60 |
| mineral substances | 1 to 3 |

Disclosed also is a method for treating acute gastrointestinal disturbances in animals with application of the composition of the invention, wherein said composition in the form of 4–6% water suspension is administered orally to the animal in the amount of from 0.2 to 0.5 g/kg of the body weight per one administration as converted to dry substance, 2–4 times a day from 30 to 60 minutes prior to feeding.

Disclosed also is a method of producing a composition for treating acute gastrointestinal disturbances in animals, wherein lignin-containing vegetable material is subjected to hydrolysis by diluted mineral acid until unhydrolyzed residue is obtained comprising from 22 to 62% by mass of hydrocellulose, said residue being then treated by 4 to 7 moduli of 0.5–1.5% alkali solution at a temperature from 20° to 100° C. during 30 to 60 minutes, washed up to neutrality, dried and ground to yield a final product.

3 Claims, No Drawings

COMPOSITION AND METHOD FOR TREATING GASTROINTESTINAL DISTURBANCES IN ANIMALS AND METHOD FOR PRODUCING THIS COMPOSITION

FIELD OF THE INVENTION

The present invention relates to veterinary medicine, and more particularly to a composition and method for treating acute gastrointestinal disturbances in animals as well as to a method for producing this composition.

BACKGROUND OF THE INVENTION

Different therapeutic compositions are used nowadays in practice for treating acute gastrointestinal disturbances in farm animals, especially young ones.

More often antibiotics are used such as, for example, tetracycline, as well as sulfamide and nitrofuran preparations, such as, for example, sulfadimidine, furazolidone and others. The effect of treatment by these preparations is not sufficiently high due to their toxicity and side effects. Moreover, in the process of treatment by antibiotics healthy microflora is destroyed alongside with deleterious one and, besides, microorganisms rather quickly get accustomed to the applied preparations.

A number of attempts are known in the art to use for treatment of acute gastrointestinal disturbances in animals preparations indifferent to the organism and detoxicating the deleterious microflora through adsorption of pathogenic microorganisms. One of such preparations is, for example, activated charcoal but it proved to be poorly effective in practice.

Early in this century there appeared some information in pertinent literature concerning the preparation based on Scholler lignin treated by alkali, used as a sorbent of pathogenic microorganisms and applied only in clinical investigation in humans as an antidiarrhea agent.

Scholler lignin obtained through pulsating percolation method, wherein the wood is treated by a diluted solution of sulfuric acid supplied in a multistage way under the temperature increase up to from 170° to 190° C. and the product of hydrolysis is periodically separated, contained from 8% to 10% by mass of hydrocellulose.

The drawback of this preparation is in the fact that due to the low content of hydrocellulose therein and viscid effect of lignin it causes bradyperistalsis thus constipating the stomach which is extremely undesirable in treating farm animals, especially young ones.

Known in the art also are lignin-containing substances used as adsorbers in biochemistry (Cf. West German Pat. No. 2532941 patented July 23, 1975). It is also suggested in this patent to use the aforementioned Scholler lignin or lignin obtained through treating the wood by super concentrated hydrochloric acid, said lignin being practically free from hydrocellulose. These preparations also exert negative effect on the intestinal peristalsis due to the absence or low content of hydrocellulose therein.

Known in the art also is a similar preparation of residual wood resulting from percolation hydrolysis by diluted solution of sulfuric acid followed by alkali treatment (Cf. USSR Inventor's Certificate No. 556811 published June 24, 1977).

Though the content of hydrocellulose in this preparation is higher as compared to that of the above mentioned preparations and reaches 10 to 19% by mass, it is still not enough to improve substantially the intestinal peristalsis and thereby therapeutic effect of said preparation.

All known above mentioned preparations containing lignin and a low amount of hydrocellulose were mainly used for humans in clinical investigations of these preparations.

Known in the art is a method for treating acute gastrointestinal disturbances in humans with application of the preparation containing 10 to 19% by mass of hydrocellulose wherein the preparation in the form of 40% water paste is administered in the amount of one table spoon 3–4 times a day prior to the meal until the termination of diarrhea.

This method was experimentally applied for treating calves suffering from disturbances of gastrointestinal tract. Some drawbacks were exposed herewith which were in the difficulty of administration of the preparation to the animal in the form of the paste as well as in the fact that the recommended dose was low for an effective treatment and the period of treatment was protracted up to from 8 to 10 days.

Known in the art is a method for producing medical preparation based on Scholler lignin (a paper by Sharkov V. I., Tsobkallo G. I. et al. in the journal "Hydroliznaja i Lesohimicheskaja Promishlennost) wherein the Scholler lignin is boiled for many hours in 2% solution of caustic soda to be washed, dried and ground thereafter. This method does not provide higher content of hydrocellulose in the final product due to its low content in the Scholler lignin. Besides, the alkaline treatment according to this method is carried out under hard conditions at which the hydrocellulose is subjected to destruction and dilution to a considerable extent which decreases its content in the product and the yield of the product as a whole.

According to another method of producing medical lignin known in the art (cf. USSR Inventor's Certificate No. 556811) hydrolized lignin obtained in the result of percolation hydrolysis of the wood is subjected to the treatment by 2–3 hydromoduli of 2% solution of caustic soda at a temperature of from 70° to 100° C. for a period of from 2 to 3 hours to be washed then with water, neutralized, dried and ground (The hydromodulus is the ratio of the mass of solution to the mass of solids to be treated).

This method does not also allow to obtain medical lignin with the content of hydrocellulose below 20% by mass is used as a raw material and, besides, the alkaline treatment is carried out in this case as well under hard conditions.

SUMMARY OF THE INVENTION

It is an object of the present invention to provide a composition with improved therapeutic properties for treating acute gastrointestinal disturbances in animals.

Another object of the present invention is to provide a composition for treating acute gastrointestinal disturbances in animals producing no side effects on the organism.

Another object of the present invention is to provide a method for treating acute gastrointestinal disturbances in animals with a higher therapeutic effect and shorter period of treatment.

Still another object of the present invention is to provide a method of producing the composition with the higher content of hydrocellulose.

With these and other objects in view there is provided a composition for treating acute gastrointestinal disturbances in animals. comprising lignin, hydrocellulose and mineral substances, i.e. ash, at the following ratio of said components in percent by mass according to the invention:

| lignin | 38 to 78 |
|---|---|
| hydrocellulose | 20 to 60 |
| mineral substances i.e. ash | 1 to 3 |

It has been suggested until now that the main adsorption properties of lignin-containing compositions are stipulated by well developed microcapillary surface of lignin which should expand along with the removal of hydrocellulose. It was experimentally found, however, that lignin-containing compositions with the higher content of hydrocellulose have even better adsorption properties relative to microorganisms, for example in *Escherichia Coli* bacteria, than pure lignin or lignin with low content of hydrocellulose. Thus lignin containing 20% by mass of hydrocellulose adsorbed 7 min, while lignin containing 60% by mass of hydrocellulose adsorbed from 14 to 16 mln of *Escherichia Coli* bacteria per 1 g of the preparation.

The therapeutic effect of this composition is based on its higher adsorption of pathogenic microorganisms and the toxins produced by these microorganisms during its passage through gastrointestinal tract and on providing hyperperistalsis of the intestine due to higher content of hydrocellulose eliminating constipation of the stomach. The latter is of particular importance when treating acute gastrointestinal disturbance in young animals, e.g. in newly born calves whose gastrointestinal tract is not yet completely developed.

Besides, the effect of the composition is also associated with the availability of different functional groups in the structure of lignin, in particular phenolic groups suppressing the activity of deleterious microorganisms. treating acute gastrointestinal disturbances in animals with a higher content of hydrocellulose is more effective than the afore said known preparation with low content of hydrocellulose (up to 20%) the evidence of which is quicker recovery of animals suffering from acute gastrointestinal disturbances without any cases of recurrence of the disease.

The proposed composition does not only regenerate the functions of the gastrointestinal tract and removes toxic substances and microorganisms therefrom but also contributes to quick regeneration of metabolic processes in the organism.

When acute gastrointestinal disturbances are treated by said composition, lignin and hydrocellulose absorb pathiogenic microorganisms and the toxins produced by these microorganisms thus preventing penetration thereof to the blood or the lymph.

It is of no less importance herewith that removal of pathogenic microorganisms and the toxins produced by them proceeds in a natural way because this composition is practically not assimilated by the organisms.

With these and other objects in view there is also provided a method of treating acute gastrointestinal disturbances in animals, wherein according to the invention a composition in the form of 4–6% water suspension is administered orally to the animals in the amount of from 0.2 to 0.5 g/kg of the body weight per one administration, as converted to dry substance, from 2 to 4 times a day from 30 to 60 minutes prior to feeding.

Administration of said composition in the form of diluted suspension considerably facilitates its application to farm animals in need thereof.

It was experimentally stated that administration of said composition in a described way promotes continuous removal of pathogenic microorganisms and the toxins produced by them from the organism and prevents their accumulation.

Implementation of the present invention by the afore described way allows to improve the therapeutic effect up to from 96 to 100% and to increase the number of recovered animals by 10–25% as compared to the method of treating with application of antibiotics, and by 5–10% as compared to the method of treating with application of lignin-containing preparations with low content of hydrocellulose (up to 20%).

With these and other objects in view there is also provided a method of producing a composition for treating acute gastrointestinal disturbances in animals, comprising hydrolyzing lignin-containing material by diluted mineral acid, treating an unhydrolyzed residue by alkali followed by washing thereof up to neutrality, drying and grinding, wherein, according to the invention, hydrolysis is carried out until the hydrolized residue is obtained containing hydrocellulose in the amount of from 22 to 62% by mass, and the unhydrolyzed residue is treated by 4–7 liquid to solid mass ratios of 0.5–1.5% alkali solution at a temperature ranging from 20 to 100% C for a period of from 30 to 60 minutes.

The conditions of hydrolysis of lignin-containing material by diluted mineral acid are chosen to be such as to yield an unhydrolized residue containing hydrocellulose from 22 to 62% by mass, this goal being achieved through varying the temperature and the duration of the process.

Soft conditions of alkaline treatment provide the composition with the higher content of hydrocellulose because in this case the destruction and solution of cellulose becomes less. This is also accompanied by an increased yield of the product as well as by decreased consumption of the reagents and expenditure of energy on heating the mass subjected to reaction. Besides, the increase in the mass ratio of alkali liquor to solid in treating the unhydrolized residue is necessary to improve the conditions of mixing and pumping over the suspension.

DETAILED DESCRIPTION OF THE PREFERABLE EMBODIMENTS

The composition for treating acute gastrointestinal disturbances in animals was studied in laboratories and under practical conditions. The object of studying was to establish the adsorption capacity of the composition and to define its effect on the function of the organism according to the clinical indices (metabolism, intestinal peristalsis etc).

Adsorption capacity of the composition for treating acute gastrointestinal disturbances in animals was determined in vitro according to the number of cells of microorganisms absorbed by one gram of the composition from the suspension of microbes. For this purpose the suspensions of microbes in a sterile physiologic solution were prepared from one-day cultures grown on solid mediums and their exact amount in a unit of volume was defined in Gorjaev's chamber. Then the total amount of microbes was adjusted to the amount suitable for calculations. After introduction of the composition into the suspension the samples of the filtrates were selected and the remaining amount of microbes therein was calculated. The amount of adsorbed microbes was then calculated by the difference between the amount of microorganisms before and after their contact with the composition. The toxicity of the composition was determined experimentally according to the clinical state of the animals. To define the toxicity different amounts of composition including those exceeding the dosage required for treatment were periodically administered orally to the animals. The period of administration ranged from one to fourteen days.

The control over the state of the organs of the animals was carried out through pathoanatomical examinations after a long period of application of the composition and consisted in visual observation over the state of mucosa of the gastrointestinal tract along the whole extension thereof as well as over the state of liver, kidneys and the blood system.

Indication to application of the composition to animals is intestinal disfunction (diarrhea).

Etiology: dyspepsia, toxic dispepsia, enterotoxemic coli-bacteriosis, anaerobic enterotoxemia.

The composition was applied to six thousand calves suffering from dyspepsia, toxic dispepsia, enterotoxemic dyspepsia, enterotoxemic coli-bacteriosis and anaerobic enterotoxemia.

The composition was put to test on 500 sucking-pigs suffering at least from one of the diseases: coli-bacteriosis, anaerobic enterotoxemia, desenteria.

The applied method of treating by said composition consisted in preparing a 4–6% water suspension of the composition and then making each sick calf drink from 100 to 300 ml, and each sick sucking-pig from 20 to 50 ml of suspension per one administration. The composition was administered from 2 to 4 times a day from 30 to 60 minutes prior to feeding. The period of treatment ranged from 2 to 5 days until complete recovery.

The experiments showed that the proposed composition with the higher content of hydrocellulose produced substantial positive effect after 2–3 administrations already.

The result of application of said composition was complete recovery of 5762 calves and 465 sucking-pigs or 96.0% and 96.5% respectively. The period of treatment ranged in average from 3 to 4 days.

No side effects such as constipation were observed with application of said composition even at the increase of the dosage by 3 or 4 times.

The additional effect of said composition is in the fact that alongside the regeneration of the function of the gastrointestinal tract and removal of toxic substances therefrom it promotes quick regeneration of metabolic processes as seen from the increase in the body weight.

The composition was applied alone and in some cases in complex with various therapeutic agents.

For the purpose of prophylaxis the proposed composition was applied to 1500 newly born cavles, the result of which was the decrease in morbidity of newly born calves by 88 to 92%.

As compared to the control group of colostrum calves and sucking-pigs treated by antibiotics and sulfamide preparations the therapeutic effect of the proposed composition was from 15 to 18% higher.

Treating the calves by the preparation with a lower content of hydrocellulose (8–12%) was found to be less effective as compared to the proposed composition and was accompanied besides by constipation of the stomach which inhibited the removal of pathiogenic microorganisms and toxins and required additional therapeutic procedures.

The percentage of recovery in this case made from 87 to 91% and the period of treatment ranged from 6 to 8 days.

The data of the tests of the composition for treating acute gastrointestinal disturbances in animals are presented in tables 1 and 2.

As it can be seen from the tables the therapeutic effect of compositions with the higher content of hydrocellulose makes from 95 to 100% as compared to 88.5% of the composition containing 12% of hydrocellulose or to from 75 to 83% of antibiotics. The most preferable are compositions containing from 25 to 40% of hydrocellulose.

TABLE I

| Hydrocellulose content in the composition, % | Results of treatment by the composition | | Results of treatment in control groups by sulfamides and antibiotics | | |
|---|---|---|---|---|---|
| | number of sick calves heads | number of recovered calves heads | % | number of sick calves heads | number of recovered calves heads | % |
| 1. 12 | 150 | 133 | 88.5 | 30 | 24 | 80.0 |
| 2. 20 | 132 | 126 | 95.4 | 40 | 33 | 82.4 |
| 3. 28 | 2977 | 2864 | 96.2 | 249 | 204 | 82.0 |
| 4. 38 | 109 | 109 | 100.0 | 94 | 76 | 80.9 |
| 5. 60 | 144 | 137 | 95.2 | 57 | 47 | 82.4 |

TABLE 2

| Hydrocellulose content in the composition, % | Results of treatment by the composition | | | Results of treatment in control group by sulfamides and antibiotics | | |
|---|---|---|---|---|---|---|
| | number of sick sucking-pigs heads | number of recovered sucking-pigs heads | % | number of sick sucking-pigs heads | number of recovered sucking-pigs heads | % |
| 1. 28 | 230 | 218 | 95.0 | 150 | 113 | 75.3 |
| 2. 38 | 270 | 260 | 96.4 | 150 | 117 | 78.0 |

A method of producing the composition for treating animals comprises hydrolysis of vegetable lignin-containing material by diluted mineral acid to yield an unhydrolized residue with a predetermined amount of hydrocellulose, which is then subjected to alkaline treatment providing required properties of the composition.

Unhydrolized residues of vegetable raw material containing from 22 to 62% by mass of hydrocellulose can be obtained through different modes of one-stage and percolation hydrolysis varying in depth of hydrolysis of cellulose, depending mainly upon the temperature and duration of the reaction.

Vegetable raw material, for example, pine or leaf-bearing wood, is subjected to percolation hydrolysis in a hydrolyzing apparatus, i.e. treated by a diluted solution of sulfuric acid gradually increasing the temperature, after preheating, from 130° to 180° C. during the period of from 0.5 to 2.5 hours. The residual wood after hydrolysis is washed with water to yield cellolignin containing from 26 to 60% by mass of hydrocellulose, depending on the period of the reaction. Besides, an unhydrolyzed residue with high content of hydrocellulose amount to from 50 to 60% by mass can be obtained through one-stage hydrolysis of wood by diluted mineral acid at a temperature ranging from 100° C. to 130°, and residue being then washed with water.

The residue left after hydrolysis is treated by 4–7 multiple amount of 0.5–1.5% alkali solution at a temperature ranging from 20° to 100° C. during 30 to 60 minutes. The obtained product is washed from alkali with water and the remainings of alkali are neutralized by diluted acetic acid, the resulting product being washed once more with water to be then dried and ground.

The final product in the dry form comprises in percent by mass:

| | |
|---|---|
| lignin | 38 to 78 |
| hydrocellulose | 20 to 60 |
| mineral i.e. ash substances | 1 to 3 |

The following typical examples will illustrate certain aspects of the present invention deliniating more clearly a method of producing the composition, the compound of the composition for treating acute gastrointestinal disturbances in animals and a method of treatment with application of said composition.

EXAMPLE I

Pine wood reduced to fragments is subjected to percolation hydrolysis in a hydrolyzing apparatus by 0.5% solution of sulfuric acid gradually increasing the temperature after preheating from 140° to 180° C. during 2 hours. The obtained product is washed with water to yield lignin containing 24% of hydrocellulose.

Unhydrolyzed residual wood is treated by 1% alkali solution in a mass ratio of 7:1 to solids at a temperature of 100° C. for 1 hour. The obtained product is washed from the alkali with water and the remaining alkali is neutralized by a diluted acetic acid, said product being then washed again with water, dried and ground. The final product comprises 20.5% of hydrocellulose, 77.0% of lignin and 2.5% of mineral (i.e. ash) substances.

EXAMPLE 2

Pine wood reduced to fragments is subjected to percolation hydrolysis in a hydrolyzing apparatus similar to that described in Example I.

The unhydrolyzed residue containing 24% of hydrocellulose is treated by 7 mass ratios of 1% alkali solution to solids at a temperature of 20° C. for one hour. Subsequent treatment is similar to that described in Example I. The obtained final product comprises 21% of hydrocellulose, 76.0% of lignin and 2.5% of mineral (i.e. ash) substances.

EXAMPLE 3

A mixture of pine and leaf-bearing wood at the ratio of 7:3 is subjected to percolation hydrolysis in a hydrolyzing apparatus similar to that described in Example I, except for duration of the reaction amounting to 100 min.

The obtained unhydrolized residue containing 30% of hydrocellulose is treated by 7 mass ratios of 1% alkali solution to solids for one hour at a temperature of 100° C.

The subsequent treatment is similar to that described in Example I.

The obtained final product comprises 27% of hydrocellulose, 70% of lignin and 3% of mineral (i.e. ash) substances.

EXAMPLE 4

Pine wood reduced to fragments is subjected to percolation hydrolysis in a hydrolyzing apparatus by 0.5% solution of sulfuric acid for 90 minutes gradually increasing the temperature after preheating from 140° to 180° C. The residual wood obtained after washing contained 35% by hydrocellulose.

The obtained product is treated by 7 mass ratios of 1% alkali solution to solids for 30 minutes at a temperature of 100° C. The resulting product is washed with water from the alkali and the remaining alkali is neutralized by diluted acetic acid, said product being then dried and ground.

The obtained final product comprises 33% of hydrocellulose, 66% of lignin and 1% of mineral (i.e. ash) substances.

EXAMPLE 5

Pine wood is subjected to percolation hydrolysis in a hydrolyzing apparatus according to the mode described in Example 4.

The obtained residual wood containing 35% of hydrocellulose is treated by 4 mass ratios of 1% alkali solution to solids for one hour at a temperature of 60° C., the remaining lignin being treated in a way similar to that described in Example 4.

The resulting final product comprises 33% of hydrocellulose, 66% of lignin and 1% of mineral (i.e. ash) substances.

EXAMPLE 6

Pine wood is subjected to one-stage hydrolysis in a hydrolyzing apparatus by 0.5% solution of sulfuric acid at a temperature of 140° C. for 40 minutes. The obtained product is washed with water to yield unhydrolyzed residue containing 1% of hydrocellulose.

The residue is treated by 7 mass ratios of 0.5% alkali solution to solids at a temperature of 20° C. for 60 minutes. The subsequent treatment is similar to that described in Example I.

The obtained final product comprises 60% of hydrocellulose, 38% of lignin and 2% of mineral (i.e. ash) substances.

EXAMPLE 7

Pine wood is subjected to one-stage hydrolysis in a hydrolyzing apparatus by 4% solution of sulfuric acid at a temperature of 100° C. for 3 hours.

The unhydrolyzed residue containing 61% of hydrocellulose is treated by 0.5% alkali solution in the amount of 7 mass ratios to solids at a temperature of 100° C. for a period of 30 minutes. The subsequent treatment is similar to that described in Example I.

The obtained final product comprises 58% of hydrocellulose, 41% of lignin, 1% of mineral (i.e. ash) substances.

EXAMPLE 8

A composition for treating acute gastrointestinal disturbances in animals containing 38% of hydrocellulose by mass was administered to a group of sucking-pigs in need thereof in the amount of 0.3 g/kg of the body weight per one administration as converted to dry substance.

The animals were made to drink the composition in the form of a 4% water suspension 3 times a day 30 minutes prior to feeding. The duration of treatment was three days. 70 out 72 sucking-pigs treated with said composition were recovered which makes 97.2%. In the control group including 70 sucking-pigs, wherein sulfamide preparations and antibiotics were applied for 5 days 54 sucking-pigs were recovered which makes 77%.

EXAMPLE 9

A composition containing 60% of hydrocellulose by mass was applied to 44 calves of colostrum period suffering from gastrointestinal disturbance.

The animals were made to drink the composition in the form of a 6% water suspension in the amount of 0.5 g/kg of the body weight per one administration, as converted to dry substance. The composition was administered 4 times a day 60 minutes prior to feeding.

43 calves out of 44 were recovered which makes 98%, the duration of treatment being from 3 to 4 days.

In the control group wherein the calves were treated by sulfamide preparations and antibiotics 32 animals out of 40 were recovered that makes 80%, the duration of treatment being from 4 to 8 days.

While the aforesaid different embodiments have been described with reference to specific particular terminology for better understanding it should be pointed out that the accepted terminology of the present invention is to no extent restrictive, each such term covering all the equivalent elements performing the same task.

Although the present invention has been described with reference to preferable standard embodiments thereof it will be understood by those skilled in the art the insignificant changes may be made in the composition and in the method of its production as well as in the method for treating acute gastrointestinal disturbances in animals without departing from the meaning of the invention.

Accordingly, all modifications and equivalents may be resorted to which fall within the spirit and scope of the invention as claimed.

What is claimed is:

1. A composition for treating acute gastrointestinal disturbances caused by pathogenic microorganism in animals, comprising 38 to 78% by mass lignin and 20 to 60% by mass hydrocellulose to form 97 to 99% by mass of said composition, said composition being prepared by treating vegetable lignin-containing material derived from pine or leaf bearing wood with dilute mineral acid to provide an unhydrolyzed residue containing from 20 to 62% by mass of hydrocellulose, treating said residue with 4 to 7 liquid to solid mass ratios of 0.5 to 1.5% alkali solution at a temperature of 20°–100° C. for 30 to 60 minutes, washing and neutralizing the resultant product with dilute acetic acid, drying and grinding.

2. A method for treating acute gastrointestinal disturbances in animals with application of the invention as set forth in claim 1, wherein said composition in the form of a 4–6% water suspension is administered to animals by drinking in the amount of from 0.2 to 0.5 g/kg of the body weight per one administration as converted to dry substance, from 2 to 4 times a day from 30 to 60 minutes prior to feeding.

3. A method for producing the composition for treating acute gastrointestinal disturbances in animals, comprising hydrolyzing lignin-containing vegetable material by diluted mineral acid to obtain an unhydrolyzed residue containing hydrocellulose in the amount of from 22 to 62% by mass;

treating the unhydrolyzed residue by 4 to 7 moduli (liquid to solid mass ratio) of 0.5–1.5% alkali solution at a temperature from 20° to 100° C. during 30 to 60 minutes, said residue being then washed up to neutrality, dried and ground to yield the final product.

* * * * *